United States Patent [19]

Dines et al.

[11] 4,374,242

[45] Feb. 15, 1983

[54] LAYERED ORGANOARSENOUS INORGANIC POLYMERS

[75] Inventors: Martin B. Dines, Santa Ana; Peter M. DiGiacomo, Mission Viejo, both of Calif.

[73] Assignee: Occidental Research Corporation, Irvine, Calif.

[21] Appl. No.: 60,078

[22] Filed: Jul. 24, 1979

[51] Int. Cl.$^3$ .................... C07F 7/00; C08G 79/00
[52] U.S. Cl. .................... 528/395; 260/429 R; 260/429.1; 260/429.2; 260/429.3; 260/429.5; 260/435 R; 260/441
[58] Field of Search ................ 260/441, 429.3, 429.1, 260/429.2, 429.5, 435, 429 R; 528/395

[56] References Cited

U.S. PATENT DOCUMENTS

| | | | |
|---|---|---|---|
| 2,312,207 | 2/1943 | Clayton et al. | 260/441 X |
| 2,476,890 | 7/1949 | Morehouse | 260/441 X |
| 3,106,509 | 10/1963 | Nagasawa | 260/441 X |

FOREIGN PATENT DOCUMENTS 170968 6/1965 U.S.S.R. .

OTHER PUBLICATIONS

Alberti et al., J. Inorg. Nucl. Chem. 40, 1113 (1978).
Maya, Inorg. Nucl. Chem. Letters, 15, 207 (1979).
Alberti, Accounts of Chem. Res. 11, 163 (1978).
Morgan, Organic Compounds of Arsenic and Antimony, Longmans, N.Y. (1918) pp. 83-89, 93-95, 105-107,120, 129-31, 142-150, 168 and 169.
Dub, Organometallic Compounds, Springer-Verlog, Berlin VIII, pp. 187-191 (1962).
Doak et al., Organometallic Compounds of Arsenic, Antimony and Bismuth, Wiley Intersc. N.Y., pp. 46-49 (1970).
Chem. Abstract 83, 70750g (1975).
Chem. Abstract 85, 13433y (1976).
Chem. Abstract 86, 155758c (1977).
Chem. Abstract 58, 1487b (1963).
Chem. Abstract 55, 11161C (1961).

*Primary Examiner*—Helen M. S. Sneed
*Attorney, Agent, or Firm*—Christie, Parker & Hale

[57] ABSTRACT

Layered organoarsenuous inorganic polymers are formed by reacting an organoarsenic acid with at least one tetravalent ion by reflux of the organoarsenic acid and the tetravalent ion in a liquid medium. There is formed a polymer in which the tetravalent metal has six coordinated bonds. The preferred tetravalent metal ions are zirconium, cerium, thorium, uranium, lead, hafnium, and titanium.

14 Claims, 8 Drawing Figures

LAYERED ORGANOARSENOUS INORGANIC POLYMERS

CROSS-REFERENCE TO RELATED APPLICATIONS

This application is related to the following copending applications: Ser. No. 945,971 filed Sept. 26, 1978, now U.S. Pat. No. 4,232,146 issued Nov. 4, 1980, of which this application is a continuation-in-part, Ser. No. 952,228 filed Oct. 17, 1978, now U.S. Pat. No. 4,235,990 issued Nov. 25, 1980, Ser. No. 966,197 filed Dec. 4, 1978, now U.S. Pat. No. 4,235,991 issued Nov. 25, 1980, Ser. No. 7,275 filed Jan. 29, 1979, Ser. No. 43,810 filed May 30, 1979 and titled Process for Preparing Layered Organophosphorus Inorganic Polymers, Ser. Nos. 54,107 and 54,097 filed July 2, 1979 and titled, respectively, Layered Cyano End Terminated Organophosphorus Inorganic Polymers and Layered Organophosphorus Inorganic Polymers Containing Mercapto or Thio Groups, and four applications filed concurrently herewith, and titled: Layered Organophosphorus Inorganic Polymers Containing Acyclic Groups, Ser. No. 60,079 Layered Organophosphorus Inorganic Polymers Containing Cyclic Groups, Ser. No. 60,250 Layered Organophosphorus Inorganic Polymers Containing Mixed Functional Groups, Ser. No. 60,249 and Layered Organophosphorus Inorganic Polymers Containing Oxygen Bonded to Carbon. The entire disclosure of each of these applications is hereby incorporated herein by this reference.

BACKGROUND OF THE INVENTION

The present invention is directed to solid inorganic polymers having organo groups anchored to the surfaces of the polymers. The majority of the polymers formed are layered crystals which display intercalation activity.

The interface surfaces of solids are responsive regions of chemical and physical action. In many practical chemical and physical phenomena such as absorption, corrosion, inhibition, heterogeneous catalysis, lubrication, ion exchange activity, adhesion and wetting and electrochemistry, activity occurs as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in their active sites which arises from the nature of their surface structure. Furthermore, much of the active sides are usually buried within the surface, and as a result of these two factors, elevated temperature and low conversions are typically encountered. Exceptions in which homogeneous catalysts are employed have been the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Efforts at heterogenizing catalysts have been discussed by Bailar, "Heterogenizing Homogeneous Catalysts," Catalysis Reviews—Sci. & Eng. 10(1) 17–35 (1974) and Hartley and Vezey, "Supported Transition Metal Complexes as Catalysts," Advances in Organometallic Chemistry 15, 189–235(1977). The entire disclosure of which is incorporated herein.

Figure 1:
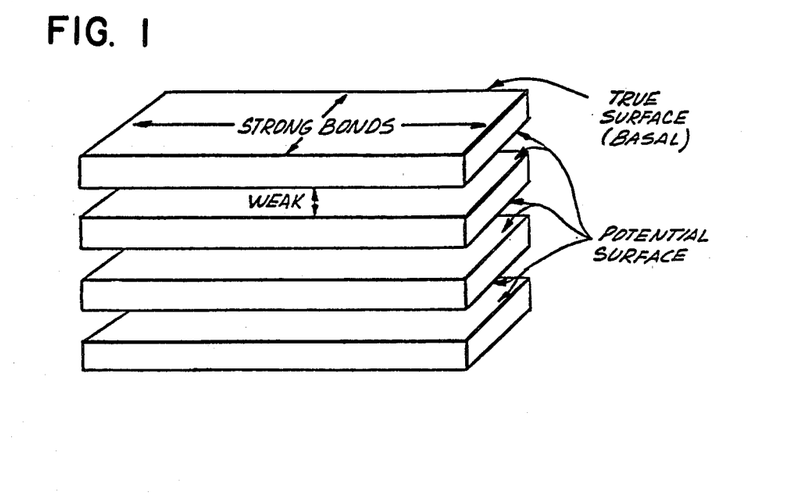
FIG. 1 illustrates a layered microcrystal. Each lamellar slab is formed of strong covalent bonds and has a thickness of about 10 atoms.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

Figure 2:
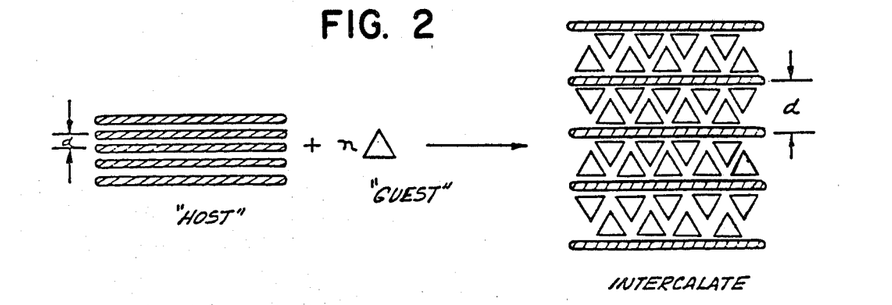
FIG. 2 illustrates intercalation where the interlayer distance is shown as "d."

In this process, designated "intercalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, this potential surface will be greater than the actual surface by a factor of the number of lamella composing the crystal. This value is typically on the order of $10^2$–$10^4$. Although edge surface is practically insignificant compared to basal surface, it is critical in the rate of intercalation, since the inclusion process always occurs via the edges. This is because bonding within the sheets is strong, and therefore, basal penetration of the sheets is an unlikely route into the crystal.

Previous studies of the intercalative behavior of layered compounds have mainly been conducted by solid-state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process on deintercalation the guests undergo only minor perturbation.

In order for a more active process to occur during intercalation, such as selective complexation or catalytic conversion, specific groups must be present which effect such activity. There might also be some preferable geometric environment about each site, as well as some optimal site-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ion or van der Waals forces of intercalated guests were operating.

Figure 3:
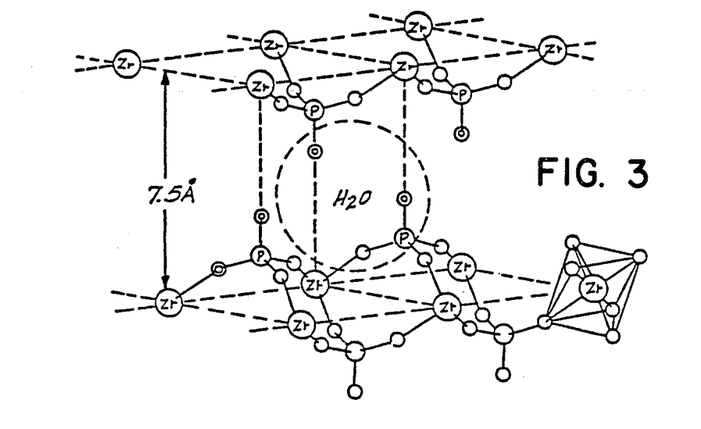
FIG. 3 illustrates the accepted structure for zirconium phosphate and spacing between layers. The dashed lines between zirconium (Zr) atoms is to establish the plane between them. In the drawing, P=phosphorus, O=oxygen, and water of hydration is shown.

One of the few layered compounds which have potential available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be promising inorganic cation exchanger for alkali, ammonium and actinide ions, Alberti, "Accounts of Chem. Research", 11, 163 (1978), incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. S. Yamaka described the reaction of this solid with ethylene oxide, which does not simply incorporate between the layers as do the other organics, but rather was found to irreversibly react with the acidic hydroxyls to form a covalently bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound inorganic alkanol groups. This conversion, while of interest, has limited if any improvement over the hydroxyls already available on zirconium phosphate.

A very recently reported effort in the field is Alberti, et al., "J. Inorg. Nucl. Chem.", 40, 1113 (1978) which is incorporated herein by reference. A method similar to that of this invention for the preparation of zirconium bis(benzenephosphonate), zirconium bis(hydroxymethanephosphonate) monohydrate, and zirconium bis(monoethylphosphate) is described, with descriptions of the properties for these products.

Following the Alberti publication, a paper by Maya appeared in "Inorg. Nucl. Chem. Letters", 15, 207 (1979), describing the preparation, properties and utility as solid phases in reversed phase liquid chromatography for the compounds $Zr(O_3POC_4H_9)_2 \cdot H_2O$, $Zr(O_3POC_{12}H_{25})_2$ and $Zr(O_3POC_{14}H_{21})_2$. All of the compositions that are described herein can be useful in gas phase, liquid phase, gas liquid, reversed phase, and bulk and thin layer chromatography. The compounds can also be useful as hosts and carriers for organic molecules and especially biologically active organic molecules (e.g. methoprene).

SUMMARY OF THE INVENTION

This invention relates to layered organoarsenous inorganic polymers. A preferred class of these compounds can be described by the following general formula:

$M^{IV}(O_3As^V—R—X)_2$, where
$M^{IV}$ is any tetravalent metal (such as $Zr^{IV}$, $Ti^{IV}$, $U^{IV}$, $Ce^{IV}$, and the like),
As is pentavalent arsenic,
R is an organo substituent (acyclic or cyclic, including heterocyclic), and
X is a halogen (F, Cl, Br, and I).

In general, these solid arsenous polymers which can be layered are useful as ion exchange agents, absorbants for organic molecules, chromatographic solid phases or supports, catalysts (especially when a Group VIII metal, such as Pt, Pd, etc., is incorporated therein, as by ion-exchange or impregnation), or as a host or carrier for controlled releases of an active ingredient, especially for biologically active organic molecules.

These arsenic-containing layered compounds are analogous to the phosphorus-containing layered compounds of the copending applications incorporated herein by reference. In general, an arsine is analogous to a phosphine, an arsenate to a phosphate, an arsonate to a phosphonate, an arsinate to a phosphinate, an arsenic compound to a phosphorus compound, and an arsenic compound to a phosphoric compound.

According to the present invention there is provided solid inorganic polymers having organo groups covalently bonded to arsenic atoms and in which the arsenic atoms are, in turn, covalently bonded by oxygen linkage to tetravalent metal atoms, and, when formed in a layered crystalline state, provide the organo groups on all of the apparent and interlamellar surfaces.

The process of preparation comprises a liquid medium reaction in which at least one organoarsenic acid compound of the formula:

$[(HO)_2OAs]_nR$ wherein n is 1 or 2, and R is an organo group covalently coupled to the arsenic atom, and wherein when n is 2, R contains at least two carbon atoms and is directly or indirectly coupled to arsenic atoms through different carbon atoms, whereby the two arsenic atoms are separated by at least two carbon atoms, is reacted with at least one tetravalent metal ion selected from the group consisting of zirconium, cerium, thorium, uranium, lead, hafnium, and titanium. The molar ratio of arsenic to the tetravalent metal is 2 to 1. Reaction preferably occurs in the presence of an excess of the organoarsenic acid compound, and the metal ion is provided as a compound soluble in the liquid medium.

Where only one specie of an organoarsenic acid compound is provided as the reactant with the tetravalent metal compound, the end product will have the empirical formula M(O₃AsR)₂. Arsenic and/or arsenous acid can also be present as reactive diluents to form part of the solid inorganic polymeric structure which is the product of the reaction. The products formed are layered crystalline to amorphous in nature. For all products, the R groups may be directly useful or serve as intermediates for the addition or substitution of other functional groups. When the product is crystalline, and n is 2, cross-linking between the interlamellar layers occurs.

The normal liquid medium is water. However, organic solvents, particularly ethanol, may be employed where water will interfere with the desired reaction. Preferably, the solvent is the solvent in which the organoarsenic acid compound is prepared. Where the organoarsenic acid compound has a sufficiently low melting point, it can serve as the liquid media.

The metathesis reaction occurs at temperatures up to the boiling point of the liquid medium at the pressures involved, typically from ambient to about 150° C., more preferably from ambient to about 100° C. While formation of the solid inorganic polymer is almost instantaneous, the degree of crystallinity of the reaction product can be increased by refluxing the reaction products for times from about 5 to 15 hours. Crystallinity is also improved by employing a sequestering agent for the tetravalent metal ion.

DETAILED DESCRIPTION

Figure 7:
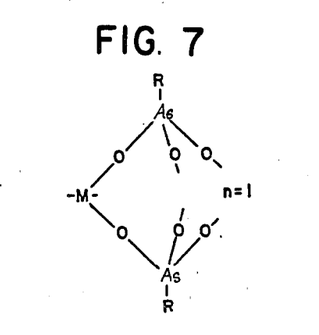
FIG. 7 shows the basic structural unit of the inorganic polymer formed by the process of the invention, where n is 1, and where As=arsenic, O=oxygen atom, M=tetravalent metal atom, and R is the organo group.
Figure 8:
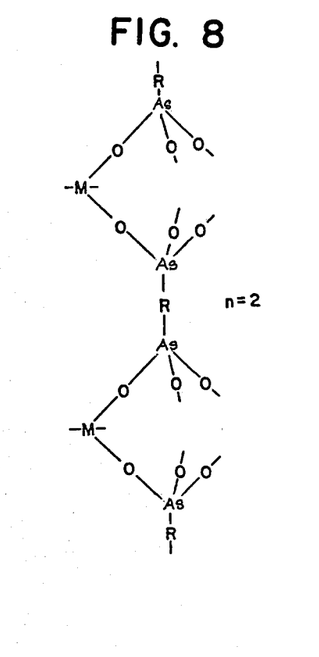
FIG. 8 shows the basic structural unit of the inorganic polymer formed by the process of the invention, where n is 2, and where As=arsenic, O=oxygen atom, M=tetravalent metal atom, and R is the organo group.

According to the present invention there is provided solid inorganic polymers in layered crystalline to amorphous state by the liquid phase metathesis reaction of at least one organoarsenic acid compound having the formula:

$$[(HO)_2OAs]_nR$$

wherein n is 1 or 2, and R is an organo group covalently coupled to the arsenic atom, with at least one tetravalent metal ion selected from the group consisting of zirconium, thorium, cerium, uranium, lead, hafnium, and titanium to form a solid inorganic polymer precipitate in which arsenic is linked to the metal by oxygen, and the organo group is covalently bonded to the arsenic atom. Where, in the organoarsenic compound, n is 2, the end product occurs in the bis configuration. In this configuration, R must contain two or more carbon atoms, preferably from two to about 20 carbon atoms, such that at least two carbon atoms separate the arsenic atoms. In this bis configuration, no single carbon atom is bound directly or indirectly to more than one [AsO(OH)₂] group. When n is 1, and as depicted in FIG. 7, the organo groups will be pendant from arsenic atoms. When n is 2, and as depicted in FIG. 8, cross-linking will occur between interlamellar surfaces of the crystalline end product. Typically, the tetravalent metal ion is provided as a soluble salt MX, wherein M is as defined above, and X is the anion(s) of the salt. The typical anions include halides, $HSO_4^{-1}$, $SO_4^{-2}$, $O_2C-CH_3^{-1}$, $NO_3^{-1}$, $O^{-2}$, and the like.

The majority of the polymeric reaction products formed are found to be layered crystalline or semi-crystalline in nature and, as such, provide layered structures similar to zirconium phosphates. The remainder are amorphous polymers possessing a large quantity of available pendant groups similar to silica gel.

By the term "organoarsenic acid compound", as used herein, there is meant a compound of the formula:

$$[(HO)_2OAs]_nR$$

wherein n is 1 or 2. R is any group which will replace a hydroxyl of arsenic acid and/or the hydrogen of arsenous acid and couple to the acid by a covalent bond. Coupling to the acid may be through carbon, oxygen, silicon, sulfur, nitrogen, and the like. Coupling through carbon or an oxygen-carbon group is presently preferred.

When, in the organoarsenic compound, n is 2, the end product occurs in the bis configuration. In this configuration, R must contain two or more carbon atoms, preferably from two to about twenty carbon atoms, such that at least two carbon atoms separate the phosphorus atoms. In this bis configuration, no single carbon atom is bound directly or indirectly to more than one [A₃O(OH)₂] group. Thus, the groups which link to the metal have the basic structural formula:

wherein R" is a bis group containing at least two carbon atoms bonded directly or indirectly to arsenic, and such that no arsenic atoms are bonded directly or indirectly to the same carbon atom. The basic structures of the inorganic polymer forms are shown in FIGS. 7 and 8.

When coupling is through carbon, the organoarsenic acid compound is an organoarsonic acid, and the product an arsonate. When coupling is through oxygen-carbon, the organoarsenic acid compound is an organoarsenic monoester acid, and the product an arsenate.

The general reaction for arsonic acids alone is shown in equation (1) below and for monoesters of arsenic acid alone by equation (2).

$$M^{+4} + 2(HO)_2OAsR \rightarrow M(O_3As-R)_2 + 4H^+ \quad (1)$$

$$M^{+4} + 2(HO)_2OAs-OR' \rightarrow M(O_3As-OR')_2 + 4H^+ \quad (2)$$

wherein R' is the remainder of the organo group.

The product contains arsenic to metal in a molar ratio of about 2 to 1, and the empirical formula for the product would show all organo groups bound to arsenic.

While nowise limiting, the R groups attachable to arsenic may be saturated and unsaturated, substituted and unsubstituted, and include, among others, alkylene, alkyloxy, alkyne, aryl, haloalkyl, alkylaryl, aryloxy, mercaptoalkyl, aminoalkyl, carboxyalkyl, morpholinoalkyl, sulfoalkyl, phenoxyalkyl, beta-diketoalkyl, cyanoalkyl, cyanoalkoxy, heterocyclics, and the like.

Figure 4:
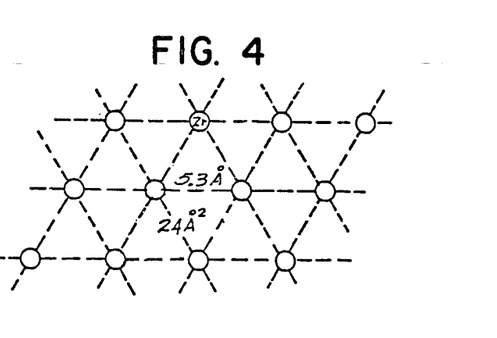
FIG. 4 illustrates a projection of zirconium plane showing accepted spacing between Zr atoms and the available linkage area.
Figure 5:
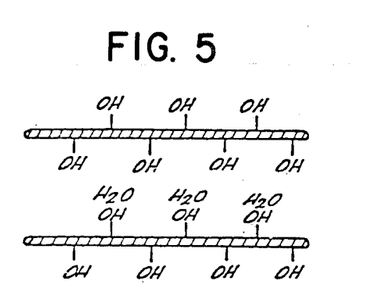
FIG. 5 is a symbolized depiction of spaced zirconium phosphate layers showing covalently bonded hydroxyl groups and water of hydration.

In general, the organo group should occupy no more than about 25 Å$^2$ to 30 Å$^2$ for proper spacing. This limitation is imposed by the basic crystal structure of zirconium arsenate (as extrapolated from data obtained with zirconium phosphate). Referring to FIG. 4, a spacing of 5.3 Å is shown between zirconium atoms in the zirconium plane of a crystal. A total area of about 25 Å$^2$ is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 25 Å$^2$, adjacent groups may be somewhat larger than 25 Å$^2$ and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE 1

| Moity | Minimum Area (Å$^2$) | Moity | Minimum Area (Å$^2$) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromethyl | 17 |
| Nitrile | 9 | Diphenylphosphine | 50(approx.) |
| Morpholinomethyl | 21 | Mercaptoethyl | 13.5 |
| Trimethylamino | 25 | | |

The process for the formation of the novel inorganic polymers is a metathesis reaction conducted in the presence of a liquid medium receptive to the tetravalent metal ion at a temperature up to the boiling point of the liquid medium, preferably from ambient to about 150° C., and more preferably, to about 100° C. at the pressure employed.

While water is the preferred liquid medium, as most of the organoarsenic acid compounds are water-soluble, an organic solvent, such as ethanol, may be employed, where water interferes with the reaction. There need only to be provided a solvent for the organoarsenic acid compound since the tetravalent ion can be dispersed as a solid in the solvent for slow release of the metal ion for reaction with the organoarsenic acid compound. If it has a sufficently low melting point, the organoarsenic acid compound may serve as a solvent. Typically, the liquid medium is the liquid medium in which the organoarsenic acid is formed.

For complete consumption of the tetravalent compound, the amount of acid employed should be sufficient to provide two moles of arsenic per mole of tetravalent metal. An excess is preferred. Arsenous acid and/or arsenic acid, if present, will enter into the reaction and provide an inorganic polymer diluted in respect to the organo group in proportion to the amount of arsenous or arsenic acid employed.

Reaction is virtually instantaneous at all temperatures leading to precipitation of layered crystalline, semi-crystalline, or amorphous inorganic polymer solid.

The amorphous phase appears as a gel similar to silica gel. The gel can be crystallized by extended reflux in the reaction medium, usually from about 5 to about 15 hours. The semi-crystalline product is characterized by a rather broad X-ray powder diffraction pattern.

The presence of sequestering agents for the metal ion slows down the reaction and also leads to more highly crystalline products. For instance, a semi-crystalline solid has been prepared by the aqueous phase reaction of zirconium chloride and excess 2-carboxyethyl phosphonic acid, followed by 15 hours of reflux. A highly crystalline modification was prepared under identical conditions, except that hydrogen fluoride was added to the reaction mixture. A slow purge of N$_2$ over the surface of the reaction solution slowly removed the fluoride from the system. Fluoride is a very strong complexing agent for zirconium ions. The slow removal of fluoride results in slow release of the metal ion for reaction with the phosphonic acid, resulting in an increase in crystallinity.

A similar enhancement of crystallinity was obtained in the reaction of thorium nitrate with 2-carboxyethyl phosphonic acid. Nitrate ion is a sequestering agent for thorium, and the rate of formation of this product is slow and the product polymer quite crystalline.

A property critical for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic polymers of this invention are also stabilized toward thermal decomposition as compared to pure organic analogs as a result of the fixation and separating effect of the inorganic support.

For zirconium chloromethyl phosphonate, for instance, weight loss did not commence until well above 400° C. The organic fragment was half lost at about 525°

C., indicating remarkable stability. Decomposition of zirconium 2-carboxyethylphosphonate begins between 300° and 400° C. The decomposition process inflection point, approximate mid-point, falls at about 400° C.

While not bound by theory, phosphates probably decompose like carboxylic esters to yield acid and unsaturates, whereas phosphonates likely form radicals by homolytic cleavage. Both nitrophenyl and cyanoethyl phosphates of zirconium decompose at about 300° C. The phenylphosphonate decomposes at about 425° C.

Besides proving the suitability of such compounds in elevated temperature applications, the TGA analysis affirmed covalent bonding to phosphorus. This is because normal intercalative interactions are reversed within 10° to 100° C. above the boiling point of the guest.

The process disclosed herein permits a wide variety of inorganic polymers to be formed having the characteristic of the organo group protected by the inorganic polymer structure and, with subsequent exchange or substitution reactions, the formation of other inorganic polymers. Polymers formed may be block, random, and the like.

For instance, a mixture of phenyl phosphonic acid and phosphorous acid was simultaneously reacted with zirconium ion to yield a single solid phase. The interlamellar distance was the same as zirconium phenyl phosphonate, or about 15.7 Å. There was no reflection at 5.6 Å, the normal spacing for zirconium phosphite. This established that the largest group should determine interlamellar distance and indicated that a discreet zirconium phosphate phase was not present. Evidence of a change in chemical environment of P-H band was established by infrared analysis. In infrared analysis of zirconium phosphite, P-H stretching is observed as a sharp band at 2470 cm$^{-1}$ (moderate intensity). In the mixed compound solid, this band was shifted to 2440 cm$^{-1}$ and broadened.

Figure 6:
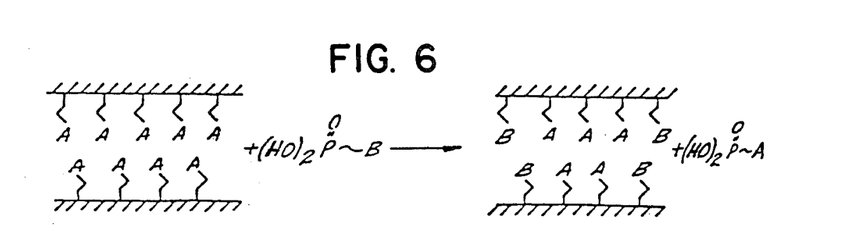
FIG. 6 illustrates an exchange reaction between anchored groups "A" and groups to be substituted for "B," and ∼ represents the portion of the organo group linking the terminal group "A" or "B" to the crystals or the organophosphorus acid compound reactant.

Another route is to exchange one pendant group for another. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis acids with tetravalent metal ions permits interlamellar cross-linking by a reaction, such as $(HO)_2OAsCH_2CH_2OAs(OH)_2 + M^{+4} \rightarrow \exists\!-\!CH_2CH_2\!-\!\models$, where, as in FIG. 6 ⊥⊥⊥⊥⊥⊥⊥ represents the interlamellar layers to which the alkyl group is anchored. As with all organo groups, for the bis configuration, at least two carbon atoms are present, preferably from two to twenty atoms, and the arsenic atoms are linked directly or indirectly to different carbon atoms. Since size of the linking group will control and fix interlamellar spacing, there is provided effective laminar sieves of fixed spacing for application analogous to that of molecular sieves.

Ion exchange activity has been established with pendant carboxylic acid groups. Prepared zirconium 2-carboxyethyl phosphonate was established to have an interlayer distance of 12.8 Å. When intercalated to form its n-hexylammonium salt, interlayer distance increased to 27.2 Å. When sodium was taken up, layer spacing increased to 14.2 Å. X-ray and infrared data indicated the highly crystalline inorganic polymer to behave as expected for carboxylic acid with behavior analogous to ion exchange resins, except that both external and internal surfaces were functional, establishing them as super surface ion exchange resins. Moreover, since the inorganic polymers can be prepared as microcrystalline powders, diffusion distances are short.

As summarized in Table 1, nitrile and mercapto anchored groups show the ability to take up silver and copper ions at room temperature for catalytic activity.

TABLE II

| Anchored Group | Metal Ion | Loading $\left(\frac{\text{mMole Metal}}{\text{mMole Zr}}\right)$ |
|---|---|---|
| —O ~ CN | 0.1 M Ag$^+$ | 0.20 |
| ~ SH | 0.1 M Ag$^+$ | 1.00 |
| —O ~ CN | 0.1 M Cu$^{++}$ | 0.10 |
| —O ~ CN | 0.1 M Cu$^{++}$ 0.5 M HOAc 0.5 M NaOAc | 0.10 |

~ = groups formed of carbon and hydrogen.
OAc = acetate radical.

The alternate to catalytic utility is to attach the metals to the organophosphorus acid prior to reaction with the soluble tetravalent metal compound.

The high surface area of the crystalline products also make them utile for sorption of impurities from aqueous and non-aqueous media.

Another utility is as an additive to the polymeric compositions. Similar to the high aspect ratio provided by solids, such as mica, which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevate heat distortion temperature. In addition, the presence of phosphorus induces flame retardant properties, as would bound halogen.

Still other utilities include solid lubricants which behave like mica, graphite, and molybdenum disulfide; solid slow release agents where intercalated materials can be slowly leached or released from the internal layers of the crystals, substances displaying electrical, optical, phase, or field changes with or without doping and the like.

While nowise limiting, the following Examples are illustrative of the preparation of solid inorganic polymers of this invention and some of their utilities.

In the Examples conducted in the atmosphere, no extraordinary precautions were taken concerning oxygen or moisture. Reagents were usually used as received from suppliers. The products formed are insoluble in normal solvents and do not sublime. However, the combined weight of yield data, spectroscopy, elemental analyses, and powder diffraction results confirm the compositions reported with good reliability.

EXAMPLE I

Preparation of: Zirconium bis para-chlorophenyl arsonate,

To a reaction flask was added 5.000 g of (HO)$_2$OAs—C$_6$H$_4$—Cl dissolved in 50 ml of dry isopropanol.

The solution was heated until the p-chlorophenyl arsonic acid was dissolved. To the solution was added a solution of 3.470 g of Zr(OC$_3$H$_7$)$_4$ dissolved in 50 ml of isopropanol. The Zr(OC$_3$H$_7$)$_4$ solution was added slowly with stirring. Upon mixing the two solutions, a precipitate appeared almost immediately. The precipitate was a light yellow white color. The reaction mixture was refluxed overnight to enhance the crystallinity of the precipitate.

Following refluxing, the reaction mixture was allowed to cool to room temperature and was filtered to recover the precipitate which had formed during refluxing. The recovered solid precipitate was washed with acetone and air-dried for about one hour on the filter funnel. The weight of the recovered Zr(O$_3$As—C$_6$H$_4$—Cl)$_2$ was 6.15 g, which was white in color to a faint yellow.

Upon infrared and X-ray diffraction analysis, the precipitate was shown to be Zr(O$_3$As—C$_6$H$_4$—Cl)$_2$.

Elemental analysis of the recovered product provided the following results. An X-ray powder diffraction pattern showed the compound to be crystalline with an interlayer spacing of 17.7 Å.

The I. R. analysis indicates the presence of aromatic bands, an arsenic-oxygen stretch, and a carbon-chlorine stretch.

|  | % C | % H |
|---|---|---|
| calculated | 25.71 | 1.43 |
| actual | 25.9 | 2.5 |

This composition can be used to adsorb organic molecules from solutions (e.g., an aqueous solution containing benzene, chloroform, and hexanol).

EXAMPLE II

Preparation of:

To a reaction flask was charged 10 g of an arsonic acid, dissolved in 50 ml of isopropanol. The solution was heated to a refluxing temperature with constant stirring. The arsonic acid was only slightly soluble in the isopropanol.

A solution was prepared of 5.96 grams of Zr(OC$_3$H$_7$)$_4$ dissolved in about 100 ml of isopropanol. This solution was added to the above-formed arsonic acid slurry.

Upon mixing the two reactants, no apparent reaction occurred. The reaction mixture was then heated for about 15 minutes, and still no apparent reaction occurred. To the reaction mixture was added 20 ml of a 48 percent solution of hydrobromic acid. The hydrobromic acid was added to help solubilize the arsonic acid. Upon addition of the hydrobromic acid, the solid in the reaction flask changed from a light pink color to a white color. Additionally, more solid began to appear in the slurry. The reaction mixture was then refluxed overnight.

Following refluxing, the reaction mixture was allowed to cool to room temperature. The mixture was filtered to recover the precipitate which had formed during refluxing. The recovered precipitate was washed with acetone and air-dried at room temperature for about one hour on the filter funnel. The solid was then dried under a vacuum for about one hour at room temperature. The solid recovered weighed 11.78 g.

Elemental analysis of the recovered product provided the following results.

|  | % C | % H | % N |
|---|---|---|---|
| expected | 30.1 | 2.5 | 4.4 |
| actual | 20.0 | 2.9 | 3.4 |

An X-ray powder diffraction pattern showed the compound to be crystalline with an interlayer spacing of about 18 Å. This composition can be used for cation exchange or as a chromatographic stationary phase.

EXAMPLE III

Preparation of:

In a reaction flask was dissolved 0.999 g of phenyl arsonic acid, which is (HO)$_2$OAs—C$_6$H$_5$, in 5 ml of water. A second solution containing 0.440 g of zirconyl oxychloride, ZrOCl$_2$, dissolved in 5 ml of water was prepared in a separate beaker.

The two solutions were combined in the reaction flask, and the reaction mixture was heated with stirring. An additional 40 ml of water was added to ensure that the arsonic acid dissolved completely. The reaction mixture was then refluxed for four hours.

After refluxing for four hours and sitting overnight, the bottom of the flask was covered with a white precipitate. The precipitate was recovered by filtering the reaction mixture through a fritted funnel. The recovered precipitate was washed with water, acetone, and ether. After the ether had air dried, the solids were dried in an oven at about 80° C. The product Zr(O$_3$A- s—$C_6H_5)_2$ weighed 0.994 g after drying. This amount of product was about an 80.6 percent yield.

Elemental analysis of the recovered product provided the following results.

|  | % C | % H |
|---|---|---|
| expected | 29.3 | 2.0 |
| actual | 30.8 | 2.7 |

An X-ray powder diffraction pattern showed the compound to be semi-crystalline with an interlayer spacing of 14.3 Å.

The composition of this Example can be used for separation of organic compounds from solution.

EXAMPLE IV

Sorption of Organics from Water

A 25 ml sample of water was saturated by contact with 5 ml of a solution of equal parts of benzene, chloroform, and 1-hexanol. Twenty ml of the saturated aqueous solution was removed and transferred to a stoppered 50 ml flask. To the solution was added 0.1 ml of ethanol as an internal standard for gas chromatographic analysis. The area ratio of each component to the standard was determined. Then 0.5 g of zirconium chlorophenyl arsonate was added with agitation. Within 30 minutes, equilibrium was established. The area ratio of each component to the standard was again determined. As is evident in the table below, the concentration of all components decreased substantially.

| Component | Relative Area before | after | % Decrease |
|---|---|---|---|
| Benzene | 0.062 | 0.0213 | 65.6 |
| Chloroform | 0.203 | 0.117 | 42.4 |

Other metal$^{+4}$ ions which are analogous to $Zr^{+4}$ in the process to make phosphate and phosphonate analogs, are metals with approximately the same ionic radius as $Zr^{+4}$ (0.8 Å), for example,

| $Zr^{+4}$ | 0.80Å | $Te^{+4}$0.81 | $Pr^{+4}$0.94 | $Mn^{+4}$0.5 |
|---|---|---|---|---|
| $W^{+4}$ | 0.66 | $Sn^{+4}$0.71 | $Pb^{+4}$0.92 | $Ir^{+4}$0.66 |
| $U^{+4}$ | 0.89 | $Si^{+4}$0.41 | $Os^{+4}$0.67 | $Hf^{+4}$0.81 |
| $Ti^{+4}$ | 0.68 | $Ru^{+4}$0.65 | $Nb^{+4}$0.67 | $Ge^{+4}$0.53 |
| $Th^{+4}$ | 0.95 | $Pu^{+4}$0.86 | $Mo^{+4}$0.68 | $Ce^{+4}$1.01 |

The thio analogs of the phosphonates and phosphates can also be made by this process. The larger, more readily redoxable elements can lead to semiconducting, photoactive supports. All of the above noted solid, layered compounds can be useful as a chromatographic solid phase, adsorbants ion-exchange and hosts or carriers for controlled release of active substances.

In the preparation of anchorable Layered Compounds, a general approach to zirconium phosphate and the other zirconium compositions described herein and in the applications incorporated herein involve the following concepts:

(1) Tetrahedral anions with 3-metal coordinating groups and one interlayer group desirable

(2) Charge on anion should be −1, −2, −3 (charge on metal ion therefore should be +2, +4, +6 for M[$O_3AY$]$_2$ stoichiometry needed for sandwiching and bridging configuration)

(i) for −1 charge, conjugate acid of anion is

"A" can be S (or Se, Cr, Mo, W, etc., (+6 forming elements)

(ii) for −2 charge, conjugate acid of anion

"A" can be P, As, Sb, V, Nb, Ta, etc., (+5 forming elements)

(iii) for −3 charge, conjugate acid of anion is

"A" can be Si, Ge, Ti, Zr, Sn, Pb (+4 forming elements).

Some exemplary salts which meet these criteria are listed below.

M[$O_3A$—Y]$_2$: Examples of compounds of structure which can form layered host structures analogous to zirconium phosphate and the phosphorus or arsenic containing compounds of the applications incorporated herein:

(1) [$O_3A$—Y]$^{-1}$ A = S, for example, Y = $NH_2$ (conjugate acid is sulfamic acid)

$M^+ = Cu^{+2}, Zn^{+2}, Fe^{+2}$, alkaline earths

(2) [$O_3A$—Y]$^{-2}$ - Zirconium phosphate prototypes (A = P, As, Sb, etc.)

(3) [$O_3A$—Y]$^{-3}$ - A = Si, for example, Y = $OCH_2CN$ $M = Mo^{+6}$

-continued

In all cases, metal ion is in octahedral sphere (could be trigonal prism)

Although the structure of these solid phases is polymeric in nature, it is convention in solid inorganic nomenclature to refer to them by their monomeric units.

Redox catalysts can be obtained when the solid inorganic polymer (e.g., organoarsenous) contains an organo-group of the quinone - hydroquinone type.

What is claimed is:

1. Process of preparing a solid, layered organoarsenous, inorganic polymer comprising reacting an organoarsenic acid with at least one tetravalent metal ion by refluxing the organoarsenic acid and tetravalent metal ion in a liquid medium.

2. The product of the process of claim 1 in which the tetravalent metal has six coordinate bonds in the polymer.

3. The process of claim 1 wherein said organoarsenic acid has the formula $[(HO)_2OAs]_nR$, wherein n is 1 or 2 and R is an organo group covalently coupled to arsenic.

4. The product of the process of claim 3 in which the tetravalent metal has six coordinate bonds in the polymer.

5. The process of claim 3 wherein the metal of said tetravalent metal ion is selected from one or more of zirconium, cerium, thorium, uranium, lead, hafnium and titanium.

6. The product of the process of claim 5 in which the tetravalent metal has six coordinate bonds in the polymer.

7. The process of claim 5 wherein the organoarsenic acid has the formula $((HO)_2OAS)_nRX$ and the product of said process is a solid organoarsenous inorganic polymer having structural units corresponding to the formula $M^{iv}(O_3As^v-R-X)_2$, where $M^{iv}$ is at least one tetravalent metal As is pentavalent arsenic, R is an organo substituent and X is a halogen.

8. A process according to claim 1, wherein said organoarsenic acid has the formula $((HO)_2OAs)_nR$, where n is 1 or 2 and R is an organo group covalently bonded to arsenic and wherein when n is 2, R contains at least two carbon atoms and is directly or indirectly coupled to arsenic atoms through different carbon atoms whereby the two arsenic atoms are separated by at least two carbon atoms, said tetravalent metal being selected from one or more of zirconium, cerium, thorium, uranium, lead, hafnium and titanium.

9. A crystalline polymer prepared by the process of claim 8 and in which the tetravalent metal has six coordinate bonds in the polymer.

10. The process of claim 8 wherein said organoarsenic acid is an organoarsonic acid and a product of said process is an arsonate, said coupling being carbon to arsenic.

11. The product of the process of claim 10 in which the tetravalent metal has six coordinate bonds in the polymer.

12. The process of claim 8 wherein said organoarsenic acid is an organoarsenic monoester acid and the product of said process is an arsenate, with arsenic-oxygen-carbon coupling.

13. A process for preparing a solid, layered organoarsenous inorganic polymer, including structural units, of the formula:

the process comprising the steps of reacting an organoarsenic acid having the formula:

with at least one tetravalent metal ion and refluxing the organoarsenic acid and tetravalent zirconium ion in a liquid medium.

14. A process of preparing a solid, layered organoarsenous inorganic polymer comprising reacting an organoarsenic acid with at least one tetravalent metal ion having an ionic radius approximately the same as the ionic radius of tetravalent zirconium and refluxing the organoarsenic acid and tetravalent metal ion in a liquid medium.

* * * * *